United States Patent [19]

Fegan et al.

[11] 4,036,253

[45] July 19, 1977

[54] GAS DILUTION DEVICE

[75] Inventors: Frank Joseph Fegan, West Orange; William Harold Smith, Rahway, both of N.J.

[73] Assignee: Peace Medical, West Orange, N.J.

[21] Appl. No.: 631,220

[22] Filed: Nov. 12, 1975

[51] Int. Cl.² ............................................. F16K 19/00
[52] U.S. Cl. .................................... 137/556; 128/210; 137/604
[58] Field of Search ................ 128/209, 210; 137/604, 137/556

[56] References Cited

U.S. PATENT DOCUMENTS

| 757,013 | 4/1904 | Bennett | 128/210 |
| 3,762,439 | 10/1973 | Heath | 137/604 X |
| 3,881,480 | 5/1975 | Lafourcade | 128/209 X |

Primary Examiner—Robert G. Nilson

[57] ABSTRACT

A gas dilution device includes a nozzle in fluid communication with selected first and second orifices disposed to direct a selected plurality of streams of a first gas at a plurality of velocities into a gas dilution chamber which is in fluid communication with a settable second gas receiving port through which an ambient second gas is drawn by the streams into the dilution chamber for diluting the first gas in a predetermined range of dilution ratios.

12 Claims, 5 Drawing Figures

GAS DILUTION DEVICE

BACKGROUND OF INVENTION

1. Field of Invention

The present invention relates to apparatus for diluting gases, and more particularly, for diluting oxygen with air.

2. Description of Prior Art

Many prior art devices are provided for diluting the concentration of oxygen supplied to patients receiving inhalation therapy. These devices comprise generally a nozzle for securing an oxygen supply tube and a venturi portion into which oxygen is directed from the nozzle. The venturi portion is coupled to atmospheric air for mixing air with the oxygen for diluting the concentration of oxygen. The supply of oxygen may be received generally from a pressurized tank or container of oxygen and in hospitals is usually received from a pressurized hospital supply system. An oxygen mask or other appliance is connected to the mixing chamber of the dilution device by a suitable conduit for delivering the diluted oxygen to the patient.

In the operation of this type of device the flow of oxygen passing from the nozzle through the venturi creates a partial vacuum in the vicinity of the oxygen stream which draws or entrains surrounding atmospheric air which is in fluid communication with the stream into the chamber. Such dilution devices are arranged to provide a single oxygen dilution ratio at a particular oxygen flow rate. The problem with this arrangement is that a separate dilution device is required for each dilution ratio specified for a given patient. Even a large number of such devices with different dilution ratios does not always satisfy medical requirements in that many patients, particularly patients with respiratory disease, have oxygen requirements which may fall somewhere in between the discreet ratios available in conventional single ratio mixing devices. An additional disadvantages of such systems is that it is costly for a user to keep on hand the quantity of dilution devices required including each dilution ratio. Necessarily each dilution device must be disconnected and reconnected in accordance with the requirements of a given patient and is thus cumbersome to implement.

To overcome some of these problems some prior art devices provide an apparatus wherein the atmospheric air inlet port is providied with a variety of aperture magnitudes thus permitting a variety of differing air volumes to be drawn into the mixing chamber by the venturi action. These devices, however, provide for selected air receiving port aperture magnitudes in discreet steps thus limiting the dilution concentration to one corresponding to the selected aperture. These devices are also limited to the range of oxygen concentrations provided. In normal usage it is desirable to provide different oxygen concentrations anywhere within the range of 24% to 100% oxygen. Even those devices with variable air inlet ports do not meet this range of concentration, in addition to being limited to discreet concentration levels. As a result a plurality of even these type of devices may be required by a user and even then not completely fulfill the medical requirements in a particular application. A further discussion of inhalation therapy devices may be found in the text Fundamentals of Inhalation Therapy by Donal F. Egan, C. V. Mosby Co., St. Louis, 1969.

SUMMARY OF INVENTION

A gas dilution device comprises a first gas receiving nozzle and a settable venturi in fluid communication with the nozzle for forming a selected first stream of the first gas at a first velocity and a selected second stream of the first gas at a second velocity. A gas mixing and delivery chamber is provided. A settable second gas receiving port including second gas restriction means is disposed in fluid communication with the chamber for selectively setting the magnitude of the flow of the second gas drawn (entrained) into the chamber through the port by the flow of the first gas. The venturi is disposed in fluid communication with and arranged to direct the streams into the chamber in a manner to draw the second gas into the chamber through the port, the volume of the second gas drawn into the chamber being determined by the first gas selected velocity and selected setting of the port whereby the first gas flowing into the chamber is mixed with and diluted with the second gas at a given dilution ratio corresponding to a selected first gas velocity and selected port restriction magnitude.

One feature of the present invention includes means for setting the second gas volume flow through the port anywhere between a maximum and minimum range.

IN THE DRAWINGS

DETAILED DESCRIPTION

Figure 2:
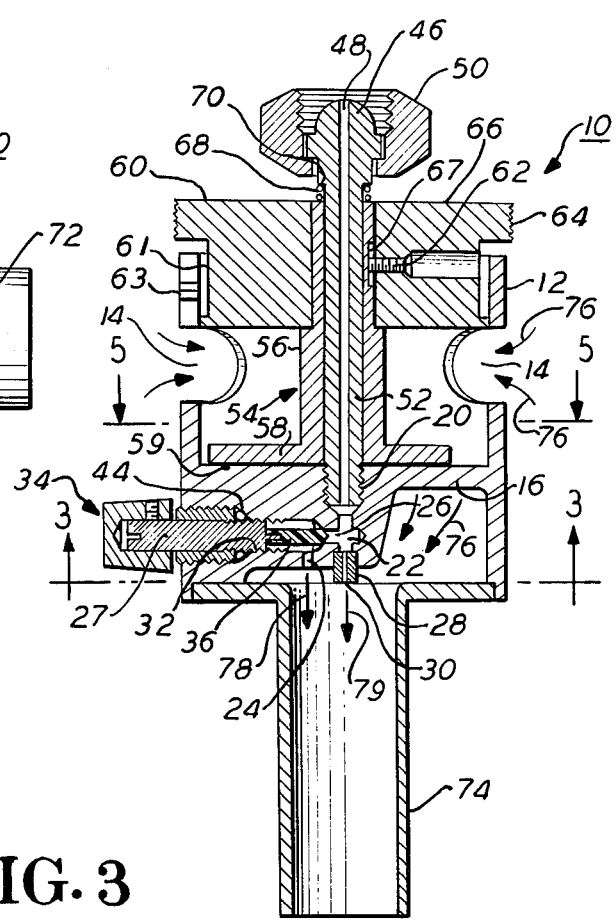
FIG. 2 is a sectional elevational view taken along lines 2—2 of FIG. 1.
Figure 3:
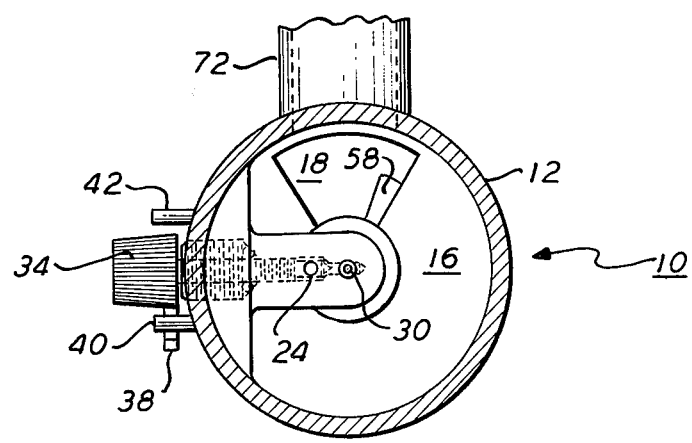
FIG. 3 is a plan sectional view taken along lines 3—3 of FIG. 2 iIlulstrating oxygen delivery orifices and air receiving port.

An oxygen dilution device 10 includes a hollow cylindrical housing 12 having a plurality of air receiving ports 14 disposed in the side walls thereof. The housing has a transverse aperture plate 16 which extends across the inner cavity of housing 12. Housing 12 includes concentration indicia indicator 63. As best seen in FIG. 3 plate 16 has an air receiving port 18 which is a segmented circular section as shown. In addition, plate 16 has a threaded bore 20 (FIG. 2) disposed on one surface thereof extending along the axial direction of housing 12. In fluid communication with the threaded bore 20 is a first axially extending bore 22 and an axially extending orifice 24 which is in fluid communication with bore 22 via a transverse connecting conduit 26. Disposed in bore 22 is an orifice insert member 28 which has disposed therein a longitudinally extending orifice 30 which extends in the same axial direction as orifice 24. Orifices 24 and 30 are both in fluid communication with bore 22. In communication with conduit 26 is a transversely extending threaded bore 32. Bore 32 receives valve closure member 34.

Member 34 has a cylindrical valve closure seat 36 which is arranged to tightly seal conduit 26 to cut off fluid communication between conduit 26 and thus, orifice 24, when seat 36 is seated. Seat 36 extends from elongated threaded pin 27 forming member 34. Member 34 when rotated opens and closes orifice 24 to bore 22 in accordance with the seated position of valve closure seat 36. Preferably member 34 and bore 32 are threaded in a manner so that bore 22 and orifice 24 are in the desired fluid communication when member 34 is rotated approximately 180°. Orifice 30 preferably has a transverse diameter corresponding to a No. 80 drill while orifice 24 has a transverse diameter corresponding to a 1/16th drill in an oxygen dilution apparatus.

Member 34 has connected thereto an orifice indicator 38 which abuts first and second tops 40 and 42 in accordance with whether seat 36 is fully seated or in the open position, respectively, Stops 40 and 42 are secured to housing 12 and limit the rotation of member 34 to between first and second orifice positions. When indicator 38 abuts stop 40 solely orifice 30 is in communication with bore 22. When indicator 38 abuts stop 42 both orifices 24 and 30 are in communication with bore 22. A suitable O-ring 44 surrounds pin 27 forming a seal with housing 12 to seal orifice 24 from the atmosphere.

Threaded into threaded bore 20 and extending along the longitudinal axis of housing 12 is stem portion 52 of oxygen delivery nozzle 46 having disposed therein a suitable oxygen delivery conduit 48. Conduit 48 is in fluid communication with and open to bore 22. A suitable nozzle connector 50 is coupled to the nozzle 46 for tightly sealing an oxygen supply line (not shown) to nozzle 46 in a conventional manner. Construction of the oxygen receiving portion of nozzle 46 and connector 50 is conventional. Stem portion 52 extends axially and centrally through housing 12 forming a cylindrical tubular member. Disposed rotatably mounted about stem portion 52 is port 18 closure and cam and dilution indicating valve 54. Valve 54 includes a stem portion 56 which is closely rotatably mounted about stem portion 52. Secured to one end of stem portion 56 is port 18 closure cam 58. Cam 58 forms a substantially gas tight seal with plate 16 at the peripheral surface 59 of cam 58 contiguous with plate 16. In this manner when cam 58 is rotated about stem portion 52 a fluid seal is maintained between cam 58 and plate 16 at the peripheral surface 59.

Figure 1:
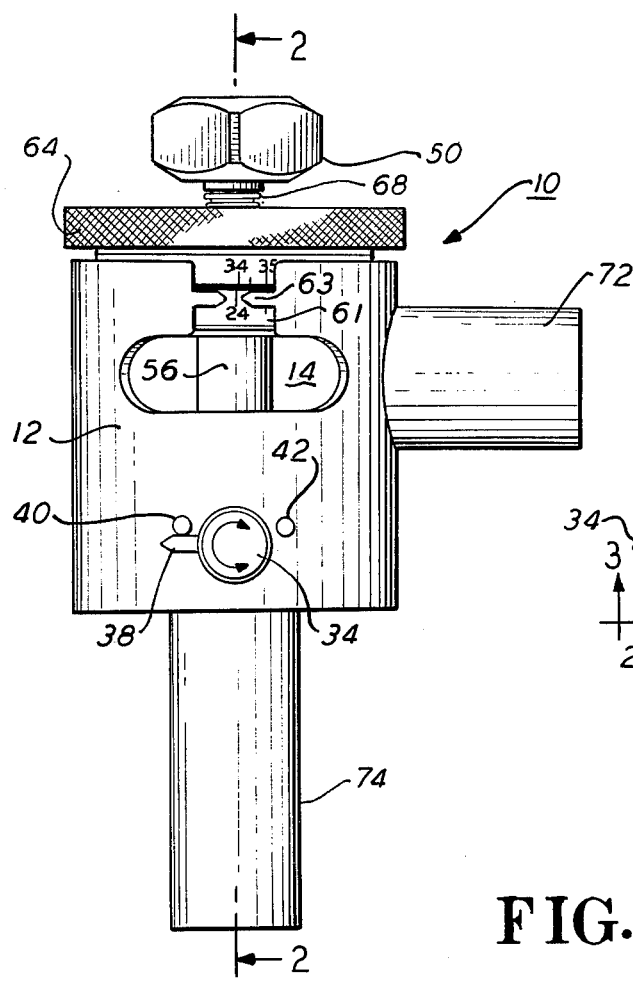
FIG. 1 is an elevational view of a device constructed and operated in accordance with an embodiment of the present invention.

To other end of stem portion 56 is secured knob and concentration indicating drum member 60. Drum member 60 is secured by suitable screw 62 is stem portion 56 at a suitably flattened segment 67 of portion 56. Drum member 60 and stem portion 56 have suitable angular position locating means, e.g., flattened segment 67 for keying the member 60 in a predetermined angular position with respect to stem portion 56 and cam 58. Member 60 is generally a cylindrical member having a knurled peripheral edge 64 by which a user may rotate member 60, the rotation of member 60 rotating in unison cam 58. Member 60 has an upper surface 66 which is resiliently coupled to connector 50 by a suitable compression spring 68 preferably, a helical cone compression spring. Spring 68 provides a relatively strong compressive force between nozzle 46 and member 60 is a manner to force cam 58 against plate 16. The compressive pressure is sufficient to maintain a gas tight seal between cam 58 and plate 16 at surface 59 while permitting member 60 to be rotated. The spring 68 can be coupled to nozzle 46 by way of a suitable shoulder 70. The friction between cam 58 and plate 16 and other frictional forces in the system maintain valve 54 in a set angular position with respect to housing 12. As shown in FIG. 1, an additional inlet port 72 is connected to the inner core of housing 12 to provide connecting means for a suitable humidifier when desired.

Depending downwardly from housing 12 and plate 16 is an air-oxygen mixing throat 74. Throat 74 is a tubular member which has a minimum suitable length which is cooperation with the orifices 24 and 30 provide an air-oxygen mixing action for mixing entrained air 76 with the oxygen streams 78 and 79 provided by respective orifices 24 and 30.

Orifice 30 is a relatively small orifice and is therefore essentially disposed antrally at the mouth of throat 74 in an arrangement to provide sufficient vacuum to insure a selected concentration of oxygen-to-air at the low end of the concentration range, i.e., 24% to 33% oxygen. In essence, since air provides approximately 21% oxygen, the oxygen provided by orifice 30 at the lower end of the range, i.e., 24%, is 3% of the total volume of the air-oxygen mixture. As provided by the apparatus of the present invention, the velocity of the oxygen through orifice 30 is sufficiently great to create a sufficient vacuum to draw air through the port 18 into the throat 74 and also provide a suitable volume of diluted oxygen at the 24% ratio. For example, this volume can be a total liter flow of 84 liters per minute with 4 liters per minute of oxygen flow. The position of the larger orifice 24 with respect to throat 74 is not as sensitive due to the larger flow and lower velocity of oxygen therethrough, but is also disposed at the mouth of throat 74. However, orifice 24 need not be centrally disposed in throat 74 mouth. It will thus be apparent that orifices 24 and 30 form with throat 74 a settable venturi having first and second oxygen stream velocities at the mouth of throat 74. The selected velocities create partial vacuums which entrain air through port 18.

As will be appreciated the seat 36 merely closes off orifice 24 to conduit 48 in the closed position while in the open position both orifices 24 and 30 are open to conduit 48. While this arrangement is preferred it will be appreciated that the orifice 30 can be closed and the orifice 24 can be opened by suitable mans (not shown) without substantially affecting the concentration ratios, i.e., the velocities of the corresponding streams. In the embodiment shown and described the volume flow of oxygen through orifice 30 is small with respect to the volume flow of oxygen through orifice 24. Thus the larger volume flow through orifice 24 effectively overrides the smaller volume flow through orifice 30. Further, the shunting action of the larger orifice 24 reduces the velocity through orifice 30.

Figure 4:
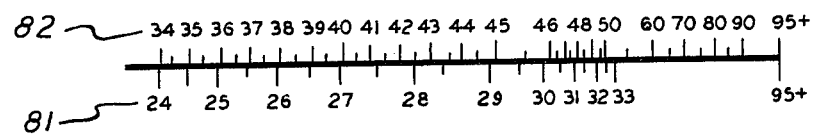
FIG. 4 illustrates oxygen concentration indicia suitable for use with the device of FIG. 1.
Figure 5:
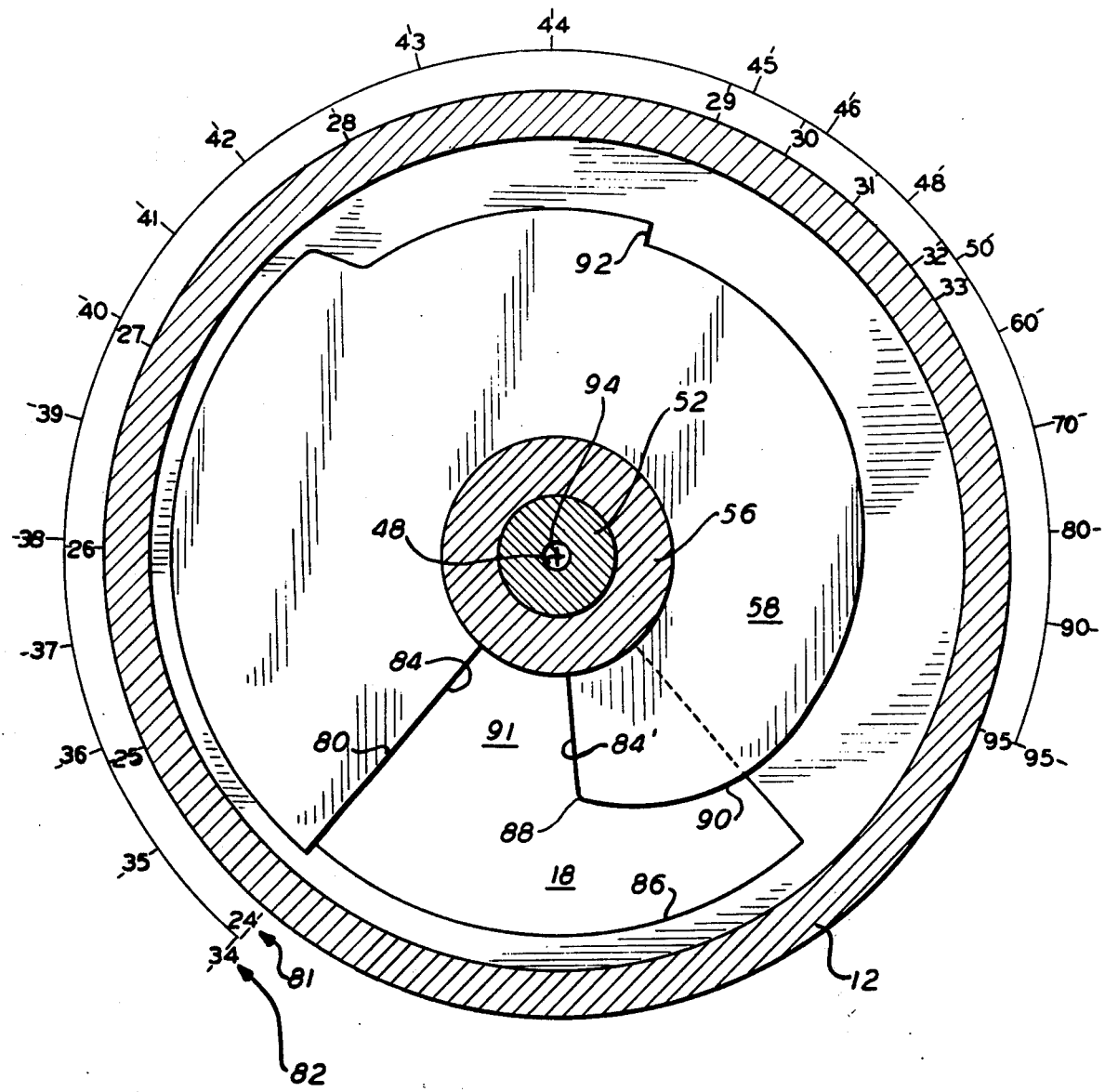
FIG. 5 is a plan sectional view taken along lines 5—5 of FIG. 2 illustrating the air receiving port closure means and the relationship of the indicia of FIG. 4 thereto.

In FIG. 5 there is shown an enlarged plan view illustrating the configuration of the cam 58 and the position of the cam to the air inlet port 18 in aperture plate 16. In addition the peripheral area round housing 12 is schematically marked in FIG. 5 with the suitable concentration indicia corresponding to the indicia of FIG. 4 to show the relative positions of the cam 58 to port 18 which provide a given oxygen dilution ratio. In FIG. 5, the position of cam 58 with respect to port 18 is shown corresponding to solely orifice 30 open to the throat 74 and a oxygen supply of approximately 50 PSI applied to nozzle 46 providing a dilution ratio of 24%. Using the cam edge 80 as a reference line, rotating the cam 58 in a clockwise direction to various angular positions so that edge 80 is radially aligned with the various concentration indicia provides a concentration ratio indicated by scale 81 ranging from 24% oxygen to 95+% wherein the most accurate calibration is evident in the range of 24 – 33% oxygen. At the 95+% setting it will be appreciated that the port 18 is completely closed except for possible small quantities of leakage of air.

A second range 82 of concentration ratios are provided when orifice 24 and orifice 30 are open in communication with throat 74. This second range of concentration varies between 34% to 95+% oxygen. The single cam 58 in cooperation with port 18 provides the proper entrained air volume for both the lower scale and upper scale of concentrations. Cam 58 includes a segmented open circular section 91 formed by edges 84 and 84' wherein edge 84 extends from the stem portion 56 radially outward to edge 80 in overlapping engagement with aperture plate 16 edge 86. Edge 84' extends approximately midway between center axis 94 and the outer peripheral edge 86 of aperture plate 16. In this example, edges 84 and 84' forms a 45° aperture or port segment. At junction 88, the edge 84' is formed into a generally radially outwardly extending spiral cam surface 90 approximately 211° from edge 84 to step 92. In the present example, cam surface 90 extends radially outwardly gradually from center axis 94 starting at junction 88 edge 84' approximately 19/32 inches increasing gradually approximately 1/64 inches every 5° from junction 88 until 155° from edge 84. Between 155° from edge 84 to 211° surface 90 is approximately 49/64 inches from the center axis 94. Between 211° and approximately 260° step 92 extends approximately 51/64 inches from center axis 94. While a specific embodiment is described it will be appreciated that modifications can be made to this cam structure and to the venturi structure by those skilled in the art for providing settable air-oxygen dilution ratios in the above-noted ranges. In particular, it is apparent that the cam configuration can vary should the orifices 24 and 30 be altered in value or number. The shape of a suitable cam, in particular cam 58 can be determined empirically using an electronic oxygen analyzer at throat 74 exit port. The analyzer analyzes the percent oxygen volume in air.

FIG. 4 illustrates actual calibration indicia secured to the periphery of drum member 60 at indicia surface 61 for indicating the desired oxygen concentration ratios at indicator 63, FIG. 1.

In operation, connector 50 is coupled to a suitable supply of oxygen under pressure such as exists in a hospital oxygen supply system. This oxygen usually is at a pressure of about 50 PSI. Throat 74 is connected to an oxygen face mask tube or oxygen tent supply tube (not shown) or other appliance for supplying the diluted oxygen under pressure to the oxygen face mask or tent as the case may be. The knurled edge 64 is rotated until the proper scale of oxygen dilution ratio on selected scales either 81 or 82 are centered at indicia indicator 63 on housing 12. Depending on whether a low ratio of oxygen dilution between 24% and 33% is desired or a higher ratio between 34 and 95+% is desired determines whether the respective scales 81 or 82 are selected.

Scale 81 provides a ratio of oxygen to air anywhere within a range of 24% to 95+%. However a therapeutically useable range of air-oxygen volume is provided in the lower portion of scale 81, more particularly, between 24% and 33% oxygen to air. Scale 82 provides a ratio of oxygen to air anywhere within a range of 34% to 95+% oxygen. This range is therapeutically useable in its entirety. By therapeutically useable is meant that for a given oxygen percentage a sufficient volume of oxygen-air mixture is provided a patient to satisfy his peak inspiratory flow rate, i.e., the peak air-oxygen volume demand of the patient.

Therefore, while a given portion of range 81 is therapeutically useful, the device provides an oxygen-air mixture throughout the range 81, but at less than desirable volume flow rate above about 33% oxygen. It is to be understood that this description is given merely by way of example. By merely altering orifice 30 magnitude, a different useful therapeutic range may be provided.

Assuming for purposes of illustration that the 24% ratio is desired, the scale 81 is selected in a manner to exhibit the numeral 24 at indicator 63. The valve closure member 34 is thus rotated to the position shown with the orifice indicator 38 abutted against stop 40. This action closes the valve closure seat 36 in conduit 26 sealing orifice 24 from bore 22. In this configuration solely orifice 30 is in communication with conduit 48 to receive the oxygen from the oxygen supply. The stream of oxygen 79 through orifice 30 creates a partial vacuum in a venturi action and entrains or draws air through port 14 and partially closed port 18 (FIG. 5) as closed off by edge 84' and surface 90 of cam 58. The air supply mixes with the oxygen stream 79 and the mixture under pressure from the stream 79 is forced through throat 74 to suitable diluted oxygen receiving means. Should any other oxygen dilution ratio be desired the knurled edge 64 is merely rotated by a user which edge is frictionally retained in position by the action of spring 68 until the desired oxygen ratio on scale 81 appears in the indicator 63 of FIG. 1. So postioning scale 81 at indicator 61 automatically positions cam 58 to close off port 18 an amount sufficient to provide the correct amount of entrained air flow through port 18 corresponding to the selected oxygen dilution ratio in cooperation with the selected orifice 30.

Should the higher oxygen ratios be desired, i.e., between 33% and 95+%, closure member 34 is rotated until orifice indicator 38 is abutted against stop 42 in a counterclockwise direction. At this time both orifices 24 and 30 are in communication with bore 22 to provide the two oxygen streams 78 and 79 respectively into throat 74. The streams 78 and 79 create a partial vacuum drawing or entraining air through port 14 and port 18 providing the selected oxygen dilution ratio. It is apparent that the higher oxygen dilution ratio is provided by way of the decreased velocity of oxygen provided by the larger orifice 24 having an effective lower velocity which effectively overrides orifice 30 as described above. To select a range of oxygen dilution ratios between 34% and 95+% the knurled edge 64 is rotated until the desired oxygen ratio appears centered in indicator 63 of FIG. 1. This adjustment automatically sets cam 58 in proper orientation with port 18 closing port 18 an amount sufficient to provide the desired entrained air flow through port 14 and port 18 in response to the venturi action of orifices 24 and 30, i.e., the vacuum created by streams 78 and 79. To insure proper mixture of the air to oxygen and prevent unwanted turbulence or black pressures, throat 74 is made a minimum suitable length as can be determined by one skilled in the fluid flow art. The calibration indicia of FIG. 4 can be appropriately located at the correct angular position on indicia surface 61 by a suitable preformed locating mark such as screw 62 to accurately position indicia calibration of FIG. 4 with respect to cam 58.

Table I shows a comparison of total liter flow with specific oxygen dilution ratios for the example described herein.

Table I

| Oxygen % | Oxygen Flow | Air Oxygen Ratio | Total Liter Flow |
|---|---|---|---|
| 24% | 4 lpm | 20:1 | 84 lpm |
| 28% | 4 lpm | 10:1 | 44 lpm |
| 35% | 8 lpm | 5:1 | 48 lpm |
| 40% | 8 lpm | 3:1 | 32 lpm |
| 47% | 10 lpm | 2:1 | 30 lpm |
| 60% | 15 lpm | 1:1 | 30 lpm |

To calculate total flow:
$B$ = oxygen flow in LPM
$A$ = air flow in LPM
$X$ = oxygen percentage
$B(100) + A(20.9) = X(A+B)$
Assume two unknowns, solve for third
$A + B$ = Total gas flow
$A/B$ = Air oxygen ratio It will thus be appreciated that an improved oxygen dilution device has been shown and described including a settable venturi which operates with a cammed aperture for providing a plurality of oxygen dilution ratios anywhere within first and second dilution ratio ranges. These first and second ranges provide a single continuous dilution range. While a particular embodiment has been described for use with a pressurized system at 50 PSI it will be appreciated that variations in orifice size, number and position may be accomplished for other values of pressurized gas flowing through conduit 48. In addition port 18 is provided with means for continuously altering the port 18 aperture size from a full open to a full closed position for a desired range of oxygen dilution ratios. A given cam and air entrainment port are settable with a plurality of oxygen stream velocities directed to the same mixing chamber for providing overlapping oxygen dilution ratios.

What is claimed is

1. A gas dilution device comprising:
   a first gas receiving nozzle,
   settable orifice means in fluid communication with said nozzle for forming a plurality of selected physically spaced streams of said first gas at a plurality of selected given velocities,
   a gas mixing and delivery chamber,
   gas receiving port means including settable gas restriction means in fluid communication with said chamber for selectively restriction the flow of a second gas drawn into said chamber through said port by the flow of said first gas, said gas restriction means including means settable anywhere within a first given range arranged to provide in cooperation with the setting of said orifice means a first gas dilution ratio settable anywhere within a second given range,
   said orifice means being disposed in fluid communication with and arranged to direct said streams into said chamber in a manner to draw said second gas into said chamber through said port, and
   means coupled to said orifice means for selectively setting said orifice means to provide a selected velocity of said first gas into said chamber, the selected velocity corresponding to the setting of said gas restriction means whereby the first gas flowing into said chamber is mixed with and diluted with the second gas at a selected dilution ratio corresponding to a given first gas velocity and corresponding gas restriction magnitude within said first range.

2. The device of claim 1 wherein said orifice means includes a first and a second orifice, said orifice setting means selectively closing at least one of said orifices to provide different first and second velocities.

3. The device of claim 1 wherein said orifice means includes a plurality of orifices each in selective separate, different spaced fluid communication with said chamber for providing simultaneous separate selected corresponding spaced streams.

4. The device of claim 2 wherein said first orifice is disposed centrally at the mouth of said chamber and said second orifice is disposed at the mouth of said chamber adjacent said first orifice, said orifices being oriented to direct said streams in substantially the same direction.

5. The device of claim 4 wherein said second orifice is larger than said first orifice in a direction transverse the direction of flow of said streams.

6. The device of claim 2 wherein said restriction means includes means coupled to said orifices to provide a gas dilution ratio anywhere within a third range when coupled with a first combination of said orifices, and a gas dilution ratio anywhere within a fourth range when coupled with a second, different combination of said orifices, said third and fourth ranges comprising the respective lower and higher contiguous portions of said second range of gas dilution ratios.

7. In combination:
   a first gas inlet nozzle,
   a plurality of orifices in concurrent spaced fluid communication with said nozzle,
   first valve means for opening and closing at least one of said orifices to provide selected streams of said first gas each selected stream having a corresponding velocity,
   a second gas inlet port in fluid communication with said orifices,
   second valve means coupled to said port for selectively opening and closing said inlet port within a first given range of aperture magnitudes, and
   a first and second gas mixing chamber in fluid communication with said orifices and with said inlet port, said orifices, chamber, and port being disposed with respect to each other so that the selected first gas streams flow into said chamber at selected corresponding velocities drawing said second gas into said chamber through said port to provide a selected first gas dilution ratio anywhere within a second given range.

8. The combination of claim 7 wherein said second valve means includes means for selectively opening and closing said inlet port anywhere within said first given range.

9. An oxygen dilution device comprising:
   a housing,
   an oxygen inlet nozzle disposed in said housing and having an oxygen delivery conduit,
   an aperture plate secured in said housing having first and second orifices in communication with said conduit for providing a plurality of oxygen streams at a plurality of velocities, said plate including an ambient air inlet port disposed adjacent said nozzle,
   a rotatable port closure cam secured contiguous with said plate and arranged to settably close said inlet port anywhere in a given range, valve means secured to said housing for closing at least one of said orifices to provide a selected oxygen stream velocity, and an air-oxygen mixing chamber disposed adjacent said orifices and inlet port for mixing air with said streams wherein said air is drawn through said inlet port into said chamber by said oxygen streams 10. The device of claim 9 wherein said housing and said cam include air-oxygen ratio indicia arranged to indicate a selected air-oxygen ratio corresponding to that selected orifice and selected inlet port magnitude setting.

11. A gas dilution device comprising:

a first gas inlet port for receiving a first gas at a given pressure, settable orifice means in fluid communication with said port for providing a first plurality of selected physically spaced parallel streams of said first gas at a second plurality of different selected given velocities, settable second gas inlet means in fluid communication with said orifice means for providing a given settable volume of entrained ambient second gas in response to the flow of a selected stream or streams of first gas having a corresponding velocity or velocities, and a gas dilution chamber in fluid communication with said inlet means and said orifice means for receiving said selected stream or streams of first gas and the selected volume of second gas corresponding to the setting of said inlet means and selected velocity.

12. A gas dilution device comprising:

a first gas receiving nozzle, a gas mixing chamber, settable orifice means including a plurality of orifices in fluid communication with said nozzle for forming a plurality of streams of said first gas at a plurality of velocities, one of said orifices being disposed centrally at the mouth of said chamber and a second of said orifices being disposed at the mouth of said chamber adjacent said one orifice, said one and second orifices being oriented to direct the corresponding streams in substantially the same direction into said chamber, a second gas receiving port including settable gas restriction means in fluid communication with said chamber for selectively restricting the flow of said second gas drawn into said chamber through said port by the flow of said first gas, said orifice means being disposed to direct said streams into said chamber in a manner to draw said second gas into said chamber through said port, and means coupled to said orifice means for selectively closing at least one of said orifices to provide selected velocities of said first gas into said chamber whereby the first gas flowing into said chamber is mixed with and diluted with the second gas at a selected dilution ratio corresponding to the selected first gas velocity and corresponding port restriction magnitude.

* * * * *